United States Patent
Tuysuzoglu et al.

(10) Patent No.: US 12,002,583 B2
(45) Date of Patent: Jun. 4, 2024

(54) UNIVERSAL HEALTH MACHINE FOR THE AUTOMATIC ASSESSMENT OF PATIENTS

(71) Applicant: SIEMENS HEALTHINEERS AG, Forchheim (DE)

(72) Inventors: Ahmet Tuysuzoglu, Jersey City, NJ (US); Dorin Comaniciu, Princeton, NJ (US); Tommaso Mansi, Plainsboro, NJ (US)

(73) Assignee: Siemens Healthineers AG, Forchheim (DE)

(*) Notice: Subject to any disclaimer, the term of this patent is extended or adjusted under 35 U.S.C. 154(b) by 460 days.

(21) Appl. No.: 17/126,408

(22) Filed: Dec. 18, 2020

(65) Prior Publication Data
US 2022/0199254 A1 Jun. 23, 2022

(51) Int. Cl.
| | |
|---|---|
| *G16H 50/20* | (2018.01) |
| *A61B 5/00* | (2006.01) |
| *G06F 16/25* | (2019.01) |
| *G06N 3/045* | (2023.01) |
| *G06N 3/08* | (2023.01) |
| *G16H 10/20* | (2018.01) |
| *G16H 10/60* | (2018.01) |
| *G16H 15/00* | (2018.01) |

(Continued)

(52) U.S. Cl.
CPC .......... *G16H 50/20* (2018.01); *A61B 5/7267* (2013.01); *G06F 16/258* (2019.01); *G06N 3/045* (2023.01); *G06N 3/08* (2013.01); *G16H 10/20* (2018.01); *G16H 10/60* (2018.01); *G16H 15/00* (2018.01); *G16H 50/30* (2018.01); *G16H 40/20* (2018.01)

(58) Field of Classification Search
CPC ........ G16H 50/20; G16H 10/60; G16H 50/30; G16H 15/00; G16H 10/20; G16H 40/67; G16H 80/00; G06F 16/25; G06F 17/60; G06N 3/04; G06N 5/04; G06N 99/00
USPC .......................................................... 705/2, 3
See application file for complete search history.

(56) References Cited

U.S. PATENT DOCUMENTS

| | | | |
|---|---|---|---|
| 11,398,299 B2* | 7/2022 | Chen ...................... | G06N 3/044 |
| 2005/0065813 A1* | 3/2005 | Mishelevich .......... | G16H 50/30 |
| | | | 705/2 |

(Continued)

OTHER PUBLICATIONS

Tang et al., "Trends and Characteristics of US Emergency Department Visits, 1997-2007," 2010, JAMA Issue No. 304, vol. 6, pp. 664-670.

(Continued)

*Primary Examiner* — Alaaeldin M Elshaer

(57) ABSTRACT

Systems and methods for automatically determining an assessment of a patient are provided. A patient is automatically interacted with, by a first trained machine learning based model, to acquire initial patient data. One or more risk factors associated with the patient are automatically determined, by a second trained machine learning based model, based on the received initial patient data. The patient is automatically interacted with, by the first trained machine learning based model, to acquire additional patient data based on the one or more determined risk factors. An assessment of the patient is automatically determined, by the second trained machine learning based model, based on the initial patient data and the additional patient data. The assessment of the patient is output.

17 Claims, 7 Drawing Sheets

(51) Int. Cl.
*G16H 50/30* (2018.01)
*G16H 40/20* (2018.01)

(56) References Cited

U.S. PATENT DOCUMENTS

| | | | |
|---|---|---|---|
| 2008/0177578 A1* | 7/2008 | Zakim | G16H 50/30 |
| | | | 705/3 |
| 2016/0283676 A1* | 9/2016 | Lyon | G16H 10/20 |
| 2017/0323064 A1* | 11/2017 | Bates | G16H 50/20 |
| 2017/0329905 A1* | 11/2017 | Passerini | G06N 5/04 |
| 2020/0005900 A1* | 1/2020 | Cha | G16B 50/00 |
| 2022/0157456 A1* | 5/2022 | Luckow | G16H 80/00 |
| 2022/0189623 A1* | 6/2022 | Breitweiser | G16H 40/67 |
| 2023/0052573 A1* | 2/2023 | Gnanasambandam | |
| | | | G16H 15/00 |

OTHER PUBLICATIONS

Kellermann, "Nonurgent Emergency Department Visits: Meeting an Unmet Need," 1994, JAMA, Issue No. 271, vol. 24, pp. 1953-1954.
Kellermann, "Crisis in the Emergency Department," 2006, New England Journal of Medicine, Issue No. 355, vol. 13, pp. 1300-1303.
Uscher-Pines, Lori, et al. "Deciding to visit the emergency department for non-urgent conditions: a systematic review of the literature." The American journal of managed care 19.1 (2013): 47.

* cited by examiner

Automatically interact with a patient, by a first trained machine learning based model, to acquire initial patient data
202

Automatically determine one or more risk factors associated with the patient, by a second trained machine learning based model, based on the acquired initial patient data
204

Automatically interact with the patient, by the first trained machine learning based model, to acquire additional patient data based on the one or more determined risk factors
206

Automatically determine an assessment of the patient, by the second trained machine learning based model, based on the initial patient data and the additional patient data
208

Output the assessment of the patient
210

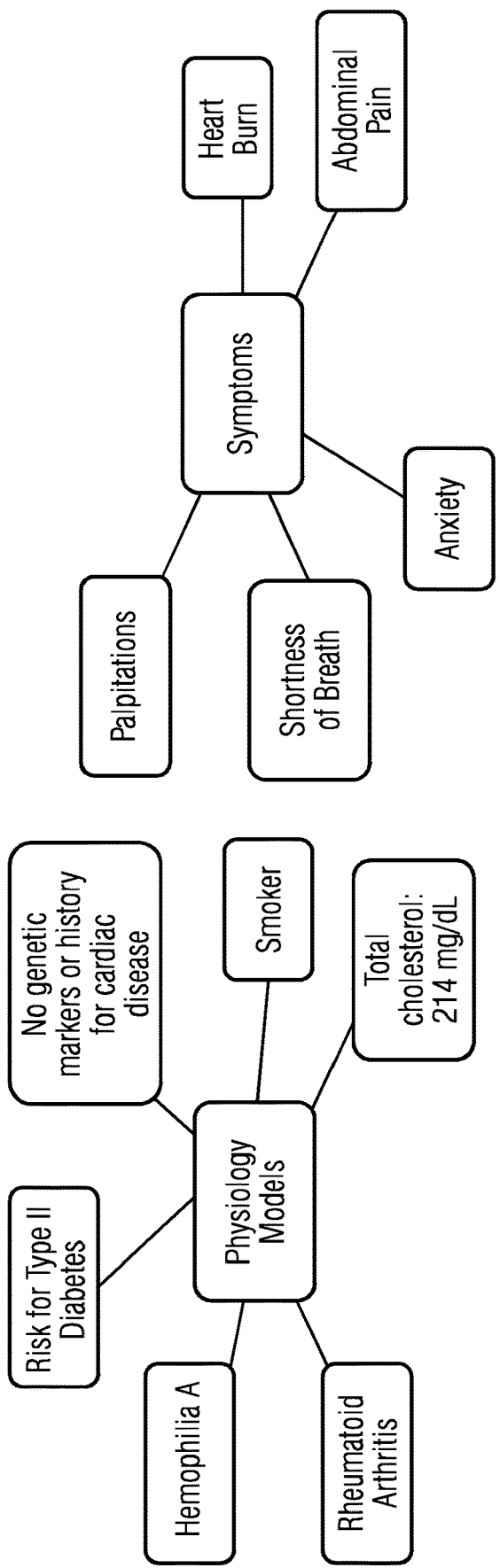

US 12,002,583 B2

UNIVERSAL HEALTH MACHINE FOR THE AUTOMATIC ASSESSMENT OF PATIENTS

TECHNICAL FIELD

The present invention relates generally to a universal health machine, and in particular to a universal health machine for the automatic assessment of patients.

BACKGROUND

Emergency departments have been treating an increasingly large number of patients in recent years. Such an increase in the number of patients visiting emergency departments has resulted in overcrowding. One major contributor to the overcrowding of emergency departments is the non-urgent use of emergency departments. Such unnecessary overcrowding of emergency departments decreases the quality of care, increases healthcare costs, and induces unnecessary pressure on healthcare professions.

BRIEF SUMMARY OF THE INVENTION

In accordance with one or more embodiments, systems and methods for the automatic assessment of patients are provided. The automatic assessment of patients in accordance with embodiments described herein may reduce the number of patients visiting emergency departments for non-urgent ailments, thereby reducing the burden on emergency departments in unnecessarily treating such patients.

In accordance with one or more embodiments, systems and methods for automatically determining an assessment of a patient are provided. A patient is automatically interacted with, by a first trained machine learning based model, to acquire initial patient data. One or more risk factors associated with the patient are automatically determined, by a second trained machine learning based model, based on the acquired initial patient data. The patient is automatically interacted with, by the first trained machine learning based model, to acquire additional patient data based on the one or more determined risk factors. An assessment of the patient is automatically determined, by the second trained machine learning based model, based on the initial patient data and the additional patient data. The assessment of the patient is output.

In one embodiment, the assessment of the patient is automatically determined by processing the initial patient data and the additional patient data into a particular format and inputting the processed initial patient data and the processed additional patient data into one or more physiology models of the patient. The assessment may be determined with an associated level of confidence. The assessment of the patient may include a diagnosis for a medical condition associated with the patient or a recommended course of action for the patient.

In one embodiment, the one or more risk factors include at least one of genetic risk factors, environmental risk factors, and lifestyle related risk factors.

In one embodiment, the second trained machine learning based model guides the automatic interaction with the patient, by the first trained machine learning based model, to acquire the additional patient data. The patient may be interacted with by asking questions to the patient and receiving answers from the patient or by retrieving clinical measurements of the patient.

These and other advantages of the invention will be apparent to those of ordinary skill in the art by reference to the following detailed description and the accompanying drawings.

BRIEF DESCRIPTION OF THE DRAWINGS

FIG. 2 shows a method for the automatic assessment of a patient, in accordance with one or more embodiments;

FIG. 3 shows an exemplary consolidated information view of risk factors, in accordance with one or more embodiments;

DETAILED DESCRIPTION

The present invention generally relates to a universal health machine for the automatic assessment of patients. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for an AI (artificial intelligence) based universal health machine to enable comprehensive point-of-care for the automatic assessment of patients. The universal health machine is a cloud-connected, integrated software and hardware system that can collect patient data from a patient and automatically determine an assessment of the health status of the patient to, for example, establish diagnoses, provide therapy recommendations, involve healthcare professions, etc. Accordingly, the universal health machine provides for 1) a digital representation of the health status of the patient at any point in time, and 2) recommended courses of action for the patient to progress from the current health status to another (e.g., healthier) health status.

Figure 1:
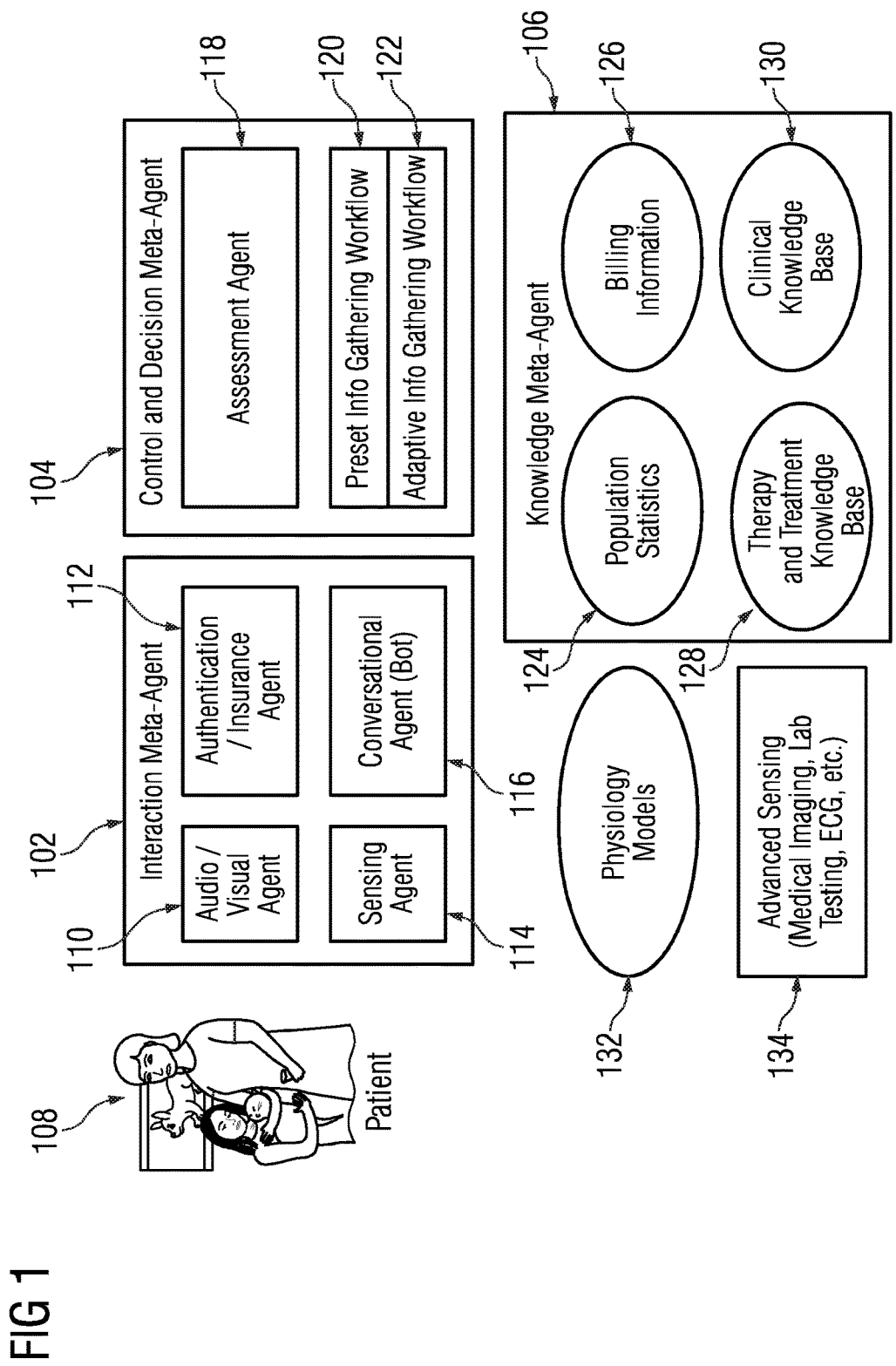
FIG. 1 shows a system architecture of a universal health machine for the automatic assessment of patients, in accordance with one or more embodiments.

FIG. 1 shows a system architecture of a universal health machine 100 for the automatic assessment of patients, in accordance with one or more embodiments. Universal health machine 100 comprises the following AI based meta-agents for the automatic assessment of patients: IMA (interaction meta-agent) 102, CDMA (control and decision meta-agent) 104, and KMA (knowledge meta-agent) 106. Each of IMA 102, CDMA 104, and KMA 106 may be implemented by a respective machine learning based model executing on one or more suitable computing devices, such as, e.g., computer 702 of FIG. 7. In general, IMA 102 is responsible for interacting with patient 108 for acquiring patient data, KMA 106 is responsible for retrieving relevant information, and CDMA 104 is responsible for 1) guiding the interaction between IMA 102 and patient 108 and guiding the retrieval of information by KMA 106 and 2) automatically determining an assessment of patient 108 based on the patient data acquired by IMA 102, the information retrieved by KMA 106, physiology models 132, and advanced sensing systems 134. Universal health machine 100 will be further described below in connection with method 200 of FIG. 2.

It should be understood that while universal health machine 100 is shown as comprising IMA 102, CDMA 104, and KMA 106, universal health machine 100 may be implemented using any number of AI based meta-agents. For example, universal health machine 100 may be implemented with less than three meta-agents by combining functionality of IMA 102, CDMA 104, and KMA 106 into less than three meta-agents or may be implemented with more than three meta-agents by dividing functionality of IMA 102, CDMA 104, and/or KMA 106 into more than three meta-agents. Further, the components of universal health machine 100 may be geographically distributed and/or maintained. By its cloud nature, universal health machine 100 may be accessed at any time and at any location (e.g., home, nursing centers, hospitals, operating rooms, etc.).

FIG. 2 shows a method 200 for the automatic assessment of a patient, in accordance with one or more embodiments. The steps of method 200 may be performed by one or more suitable computing devices, such as, e.g., computer 702 of FIG. 7. Method 200 will be described with continued reference to universal health machine 100 of FIG. 1. In one example, the steps of method 200 are performed by universal health machine 100 of FIG. 1.

At step 202 of FIG. 2, a patient (or any other user) is automatically interacted with, by a first trained machine learning based model, to acquire initial patient data. In one example, the first trained machine learning based model is IMA 102 of FIG. 1 automatically interacting with patient 108 to acquire the initial patient data. IMA 102 may automatically interact with patient 108 by, e.g., asking questions and receiving answers from patient 108, gathering clinical measurements from patient 108 using one or more sensors, etc. The initial patient data may include patient identification information used to uniquely identify patient 108, clinical data associated with patient 108, or any other relevant data associated with patient 108. The functionality of IMA 102 for acquiring patient data from patient 108 is represented by various human-machine agents in FIG. 1. As shown in FIG. 1, IMA 102 comprises audio/visual agent 110, authentication/insurance agent 112, sensing agent 114, and conversational agent (bot) 116.

Audio/visual agent 110 and conversational agent 116 are configured to communicate with patient 108 by, e.g., asking patient-relevant questions to patient 108 and understanding the answers to those questions from patient 108, which are then communicated to CDMA 104. In particular, conversational agent 116 is configured to facilitate communication (e.g., spoken or written) between IMA 102 and patient 108 using, e.g., natural language processing or any other suitable technique. Audio/visual agent 110 is configured to acquire observed data of patient 108 via sensors such as, e.g., cameras, microphones, etc. The observed data of patient 108 may include, e.g., body language, mood, skin appearance, tone and sound of the voice, etc. Audio/visual agent 110 also creates virtual avatars for more natural interaction with patient 108.

Sensing agent 114 is configured to retrieve clinical measurements of patient 108 via one or more sensors and communicate the clinical measurements to CDMA 104. The clinical measurements may include vitals and other health measurements, such as, e.g., blood pressure, pulse rate, temperature, breathing rate, breath analysis, oxygen saturation, wearable device sensing. The clinical measurements may be acquired using any suitable sensors, such as, e.g., wearable devices, electrophysiology sensing probes, cuffs, vests, stiffness sensing ultrasound systems, x-ray detectors for limbs, finger pricking/blood withdrawal stations, throat/nose swab tests, palpations for lymph nodes, urine analyzers, etc. Sensing agent 114 may be extended to retrieve clinical measurements of patient 108 using new sensing technologies as they become available.

Authentication/insurance agent 112 is configured to identify patient 108 from the patient identification information. Authentication/insurance agent 112 associates patient 108 with a universal unique patient ID (identifier), which is used to access and retrieve data associated with patient 108 from various patient databases, such as, e.g., electronic medical record databases, healthcare provider databases, insurance provider databases, etc.

At step 204 of FIG. 2, one or more risk factors associated with the patient are automatically determined, by a second trained machine learning based model, based on the acquired initial patient data. In one example, the second trained machine learning based model is CDMA 104 of FIG. 1.

The functionality of CDMA 104 for determining the risk factors associated with patient 108 is represented by various agents in FIG. 1. As shown in FIG. 1, CDMA 104 comprises assessment agent 118 (as well as preset information gathering workflow agent 120 and adaptive information gathering workflow agent 122, discussed below in connection with step 206 of FIG. 2). Assessment agent 118 combines the initial patient data (acquired at step 202) together with other patient data from physiology models 132 associated with patient 108, from advanced sensing systems 134, from KMA 106, or any other patient data. Assessment agent 118 then determines the risk factors associated with patient 108 based on the combined patient data using physiology models 132. The risk factors may include, e.g., genetic risk factors, environmental risk factors, lifestyle related risk factors, risk factors associated with prior clinical conditions, or any other relevant risk factors. The genetic risk factors may be quantitatively determined based on the analysis of genetic material or based on the family history of patient 108 (if genetic information is not available). Environmental risk factors may be associated with the demographical and geographical information, such as, e.g., countries that patient 108 has been to, ongoing epidemics, etc. Lifestyle related risk factors may be determined from information on patient behavior, such as, e.g., smoking, alcohol consumption, drug usage, etc.

Physiology models 132 comprises one or more physiology models modelling physiological function or operation of patient 108. In one embodiment, physiology models 132 comprises a collection of physiology models each modeling the physiological function or operation of a specific anatomical object (e.g., an organ, tissue, and/or disease). Physiology models 132 combine the initial patient data, such as, e.g., genetic information (including the presence of known markers for any diseases), lifestyle choices, environmental information, demographic information, lab tests, medical images, or any other relevant data associated with patient 108. Physiology models 132 then simulate various clinical scenarios. Physiology models 132 may comprise statistical models (e.g., neural networks such as, e.g., Deep Profiler), computational physics-based models (e.g., constitutive laws of organ systems whose parameters may be personalized with patient-specific parameters determined based on the initial patient data), or any other suitable model for modelling the physiology of patient 108. The Deep Profiler is further described in U.S. Patent Publication No. 2019/0371450, filed Feb. 8, 2019, the disclosure of which is incorporated by reference herein in its entirety.

Advanced sensing system 134 represents lab tests, medical imaging, pathology, and other patient sensing devices (e.g., ECG (electrocardiograph)) that cannot be performed at the point-of-care and require specialized settings.

KMA 106 provides on-demand current health related information to CDMA 104 for improved decision making. The health related information may include, e.g., population statistics 124, billing information 126, therapy and treatment knowledge base 128, clinical knowledge base 130, or any other relevant health related information. KMA 106 is continuously updated over time with new health related information. KMA 106 may be based on, for example, a knowledge graph constructed using standard ontologies and data representations.

In one embodiment, assessment agent 118 generates a consolidated information view of the determined risk factors. The consolidated information view is a human-interpretable interactive graphical display of the determined risk factors. FIG. 3 shows an exemplary consolidated information view 300 of risk factors, in accordance with one or more embodiments. Consolidated information view 300 shows various risk factors determined from physiology models and various risk factors determined from symptoms identified from the patient. Items in consolidated information view 300 may be colored and clustered together for ease of interpretation.

At step 206 of FIG. 2, the patient is automatically interacted with, by the first trained machine learning based model, to acquire additional patient data based on the one or more determined risk factors. IMA 102 may interact with patient 108 by, e.g., asking questions and receiving answers from patient 108, gathering clinical measurements from patient 108 using one or more sensors, etc. The additional patient data may include clinical data associated with patient 108 or any other relevant data associated with patient 108. To facilitate the interaction between patient 108 and IMA 102, the consolidated information view of the determined risk factors, generated by assessment agent 118, may be presented to patient 108.

The interaction between patient 108 and IMA 102 is guided by preset information gathering workflow agent 120 and/or adaptive information gathering workflow agent 122 of CDMA 104 based on the determined risk factors. Preset information gathering workflow agent 120 provides a preset workflow for gathering information from patient 108. The preset workflow may be determined based on, e.g., current clinical knowledge and existing workflows. Adaptive information gathering workflow agent 122 provides an adaptive workflow for gathering information from patient 108. The adaptive workflow is personalized based on the current health status and health history of patient 108, as well as real time on-going interaction between patient 108 and IMA 102. Preset information gathering workflow agent 120 and/or adaptive information gathering workflow agent 122 of CDMA 104 guide the patient interaction of audio/visual agent 110 and conversational agent 116 of IMA 102 for asking questions to patient 108 and the patient interaction of sensing agent 114 for automatically acquiring patient measurements. Accordingly, CDMA 104 may receive patient data from IMA 102 and request new patient data from IMA 102 based on, e.g., data required by physiology models 132 to thereby acquire patient data sufficient for determining an assessment of patient 108. The bidirectional communication between patient 108 and IMA 102 is important for refining the understanding of the health status of patient 108.

Figure 4:
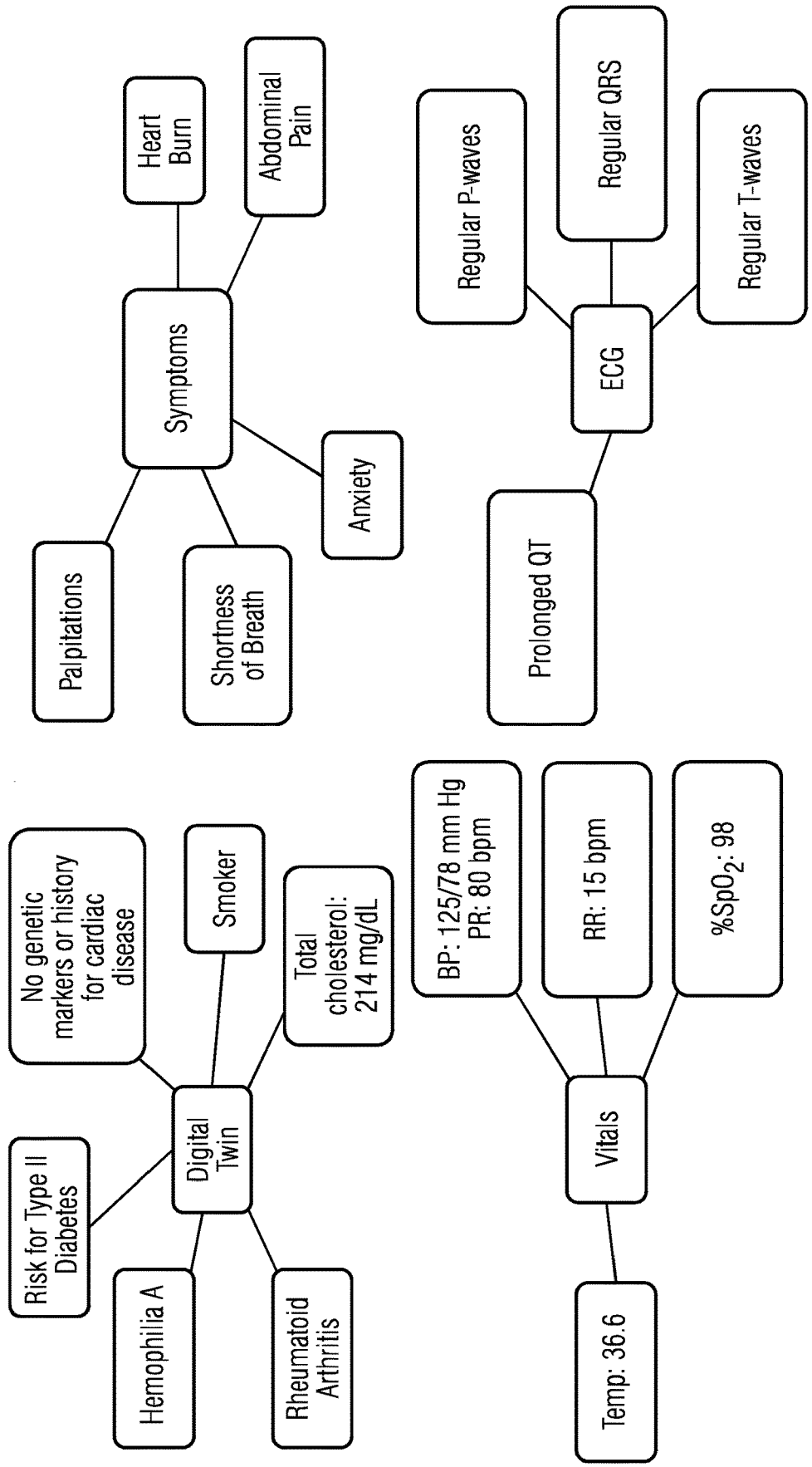
FIG. 4 shows an exemplary updated consolidated information view of risk factors, in accordance with one or more embodiments.

As the additional patient data is acquired, the consolidated information view may be updated based on the additional patient data. FIG. 4 shows an exemplary updated consolidated information view 400 of risk factors, in accordance with one or more embodiments. Consolidated information view 400 is updated from consolidated information view 300 of FIG. 3 based on the additional patient data. Consolidated information view 400 is updated to show vitals and ECG patient data. Consolidated information view 400 may be presented to the patient and updated as the additional patient data is acquired to further facilitate interaction between patient 108 and IMA 102.

At step 208 of FIG. 2, an assessment of the patient is automatically determined, by the second trained machine learning based model, based on the initial patient data and the additional patient data. The assessment of the patient may be determined using the second trained machine learning based model utilized at step 204. In one example, CDMA 104 of FIG. 1 automatically determines the assessment of patient 108 based on the initial patient data and the additional patient data. The patient data (initial and additional patient data) acquired by IMA 102 is in a raw format. Assessment agent 118 processes the raw patient data (or has the raw patient data processed via a cloud based system) into a standard format suitable for input into physiology models 132. Once processed, the processed patient data is input into physiology models 132 for simulating various clinical scenarios and determining an assessment of patient 108.

The assessment may comprise a diagnosis for a medical condition associated with patient 108, recommended courses of action (e.g., for therapy or for seeking assistance from a medical professional) for progressing patient 108 from its current health status to a target (e.g., better) health status, or any other assessment of patient 108. In one example, assessment agent 118 may determine that a medical condition of patient 108 is not significant and recommend that patient 108 either do nothing or suggest proper treatment. In another example, assessment agent 118 may determine that a medical condition of patient 108 is of moderate significance and recommend proper treatment and schedule a follow-up appointment with universal health machine 100. In another example, assessment agent 118 may determine that a medical condition of patient 108 is significant and recommend that patient 108 schedule an appointment with a healthcare professional while sharing the assessment with the healthcare professional. In another example, assessment agent 118 may determine that the assessment of a medical condition of patient 108 is ambiguous but has risk and recommend that patient 108 schedule an appoint with a healthcare professional while sharing the assessment with the healthcare professional. In another example, assessment agent 118 may determine that the assessment of a medical condition of patient 108 is ambiguous but does not have immediate risk and recommend that patient 108 schedule an appoint with a healthcare professional while sharing the assessment with the healthcare professional. While recommending that patient 108 schedule an appointment with a healthcare professional, assessment agent 118 may suggest one or more open time slots for the appointment.

In one embodiment, assessment agent 118 may provide the assessment with an associated level of confidence (e.g., represented as a probability) to facilitate decision making by patient 108.

At step 210, the assessment of the patient is output. For example, the assessment of the patient can be output by displaying the assessment of the patient on a display device of a computer system, verbally narrating the assessment of the patient via speakers on a computer system, storing the assessment of the patient on a memory or storage of a computer system, or by transmitting the assessment of the patient to a remote computer system. In one embodiment, the assessment of the patient is output to the patient using the first trained machine learning based model utilized at step 202. In one example, audio/visual agent 110 of IMA 102 outputs the assessment to patient 108 by displaying the assessment or by verbally narrating the assessment to patient 108. In another embodiment, the assessment of the patient is automatically transmitted to a healthcare professional associated with patient 108.

In one embodiment, universal health machine 100 may continually interact with patient 108 over time to thereby progressively build a consolidated "life-long" representation of the health status of patient 108. Universal health machine 100 may be utilized for determining an assessment of patient 108 for any medical condition, such as, e.g., performing rapid testing of diseases and other ailments during a epidemic outbreak, performing routine annual checkups, etc.

In one embodiment, universal health machine 100 may be implemented with a hybrid approach, where one or more healthcare professionals are involved at one or more steps performed by universal health machine 100. For example, one or more medical professionals may be involved in determining the risk factors (step 204 of FIG. 2) or determining the assessment of the patient (step 208 of FIG. 2).

In one embodiment, a healthcare professional associated with patient 108 may be provided with a graphical user interface to enable the healthcare professional to retrieve and act based on the assessment or other data in universal health machine 100, thereby enabling two-sided services between patient 108 and the healthcare professional.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems for utilizing various machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in the embodiments described herein can be adapted by methods and systems for training the machine learning based. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 5:
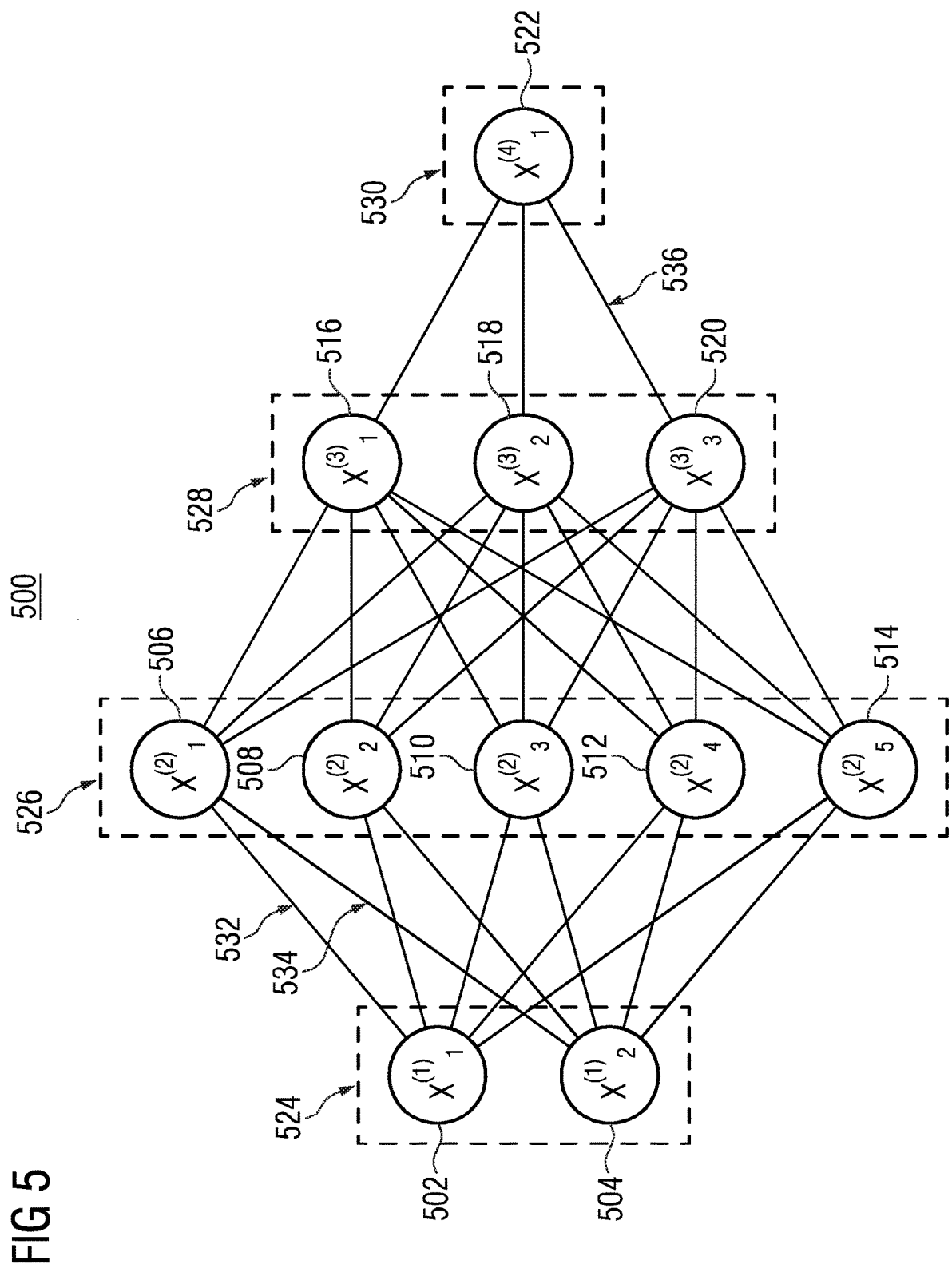
FIG. 5 shows an exemplary artificial neural network that may be used to implement one or more embodiments.

FIG. 5 shows an embodiment of an artificial neural network 500, in accordance with one or more embodiments. Alternative terms for "artificial neural network" are "neural network", "artificial neural net" or "neural net". Machine learning networks described herein, such as, e.g., the machine learning based model implementing IMA 102, CDMA 104, and KMA 106 in FIG. 1, may be implemented using artificial neural network 500.

The artificial neural network 500 comprises nodes 502-522 and edges 532, 534, . . . , 536, wherein each edge 532, 534, . . . , 536 is a directed connection from a first node 502-522 to a second node 502-522. In general, the first node 502-522 and the second node 502-522 are different nodes 502-522. For example, in FIG. 5, the edge 532 is a directed connection from the node 502 to the node 506, and the edge 534 is a directed connection from the node 504 to the node 506. An edge 532, 534, . . . , 536 from a first node 502-522 to a second node 502-522 is also denoted as "ingoing edge" for the second node 502-522 and as "outgoing edge" for the first node 502-522.

In this embodiment, the nodes 502-522 of the artificial neural network 500 can be arranged in layers 524-530, wherein the layers can comprise an intrinsic order introduced by the edges 532, 534, . . . , 536 between the nodes 502-522. In particular, edges 532, 534, . . . , 536 can exist only between neighboring layers of nodes. In the embodiment shown in FIG. 5, there is an input layer 524 comprising only nodes 502 and 504 without an incoming edge, an output layer 530 comprising only node 522 without outgoing edges, and hidden layers 526, 528 in-between the input layer 524 and the output layer 530. In general, the number of hidden layers 526, 528 can be chosen arbitrarily. The number of nodes 502 and 504 within the input layer 524 usually relates to the number of input values of the neural network 500, and the number of nodes 522 within the output layer 530 usually relates to the number of output values of the neural network 500.

In particular, a (real) number can be assigned as a value to every node 502-522 of the neural network 500. Here, $x^{(n)}_i$ denotes the value of the i-th node 502-522 of the n-th layer 524-530. The values of the nodes 502-522 of the input layer 524 are equivalent to the input values of the neural network 500, the value of the node 522 of the output layer 530 is equivalent to the output value of the neural network 500. Furthermore, each edge 532, 534, . . . , 536 can comprise a weight being a real number, in particular, the weight can be a real number within the interval [−1, 1] or within the interval [0, 1]. Here, $w^{(m,n)}_{i,j}$ denotes the weight of the edge between the i-th node 502-522 of the m-th layer 524-530 and the j-th node 502-522 of the n-th layer 524-530. Furthermore, the abbreviation $w^{(n)}_{i,j}$ is defined for the weight $w^{(n,n+1)}_{i,j}$.

In particular, to calculate the output values of the neural network 500, the input values are propagated through the neural network. In particular, the values of the nodes 502-522 of the (n+1)-th layer 524-530 can be calculated based on the values of the nodes 502-522 of the n-th layer 524-530 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smooth step function) or rectifier functions.

In particular, the values are propagated layer-wise through the neural network, wherein values of the input layer 524 are given by the input of the neural network 500, wherein values of the first hidden layer 526 can be calculated based on the values of the input layer 524 of the neural network, wherein values of the second hidden layer 528 can be calculated based in the values of the first hidden layer 526, etc.

In order to set the values $w^{(m,n)}_{i,j}$ for the edges, the neural network 500 has to be trained using training data. In particular, training data comprises training input data and training output data (denoted as $t_i$). For a training step, the neural network 500 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 500 (backpropagation algorithm). In particular, the weights are changed according to $$w'^{(n)}_{i,j} = w^{(n)}_{i,j} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (y_k^{(n+1)} - t_j^{(n+1)}) \cdot f'(\Sigma_i x_i^{(n)} \cdot w_{i,j}^{(n)})$$

if the (n+1)-th layer is the output layer 530, wherein f' is the first derivative of the activation function, and $y^{(n+1)}_j$ is the comparison training value for the j-th node of the output layer 530.

Figure 6:
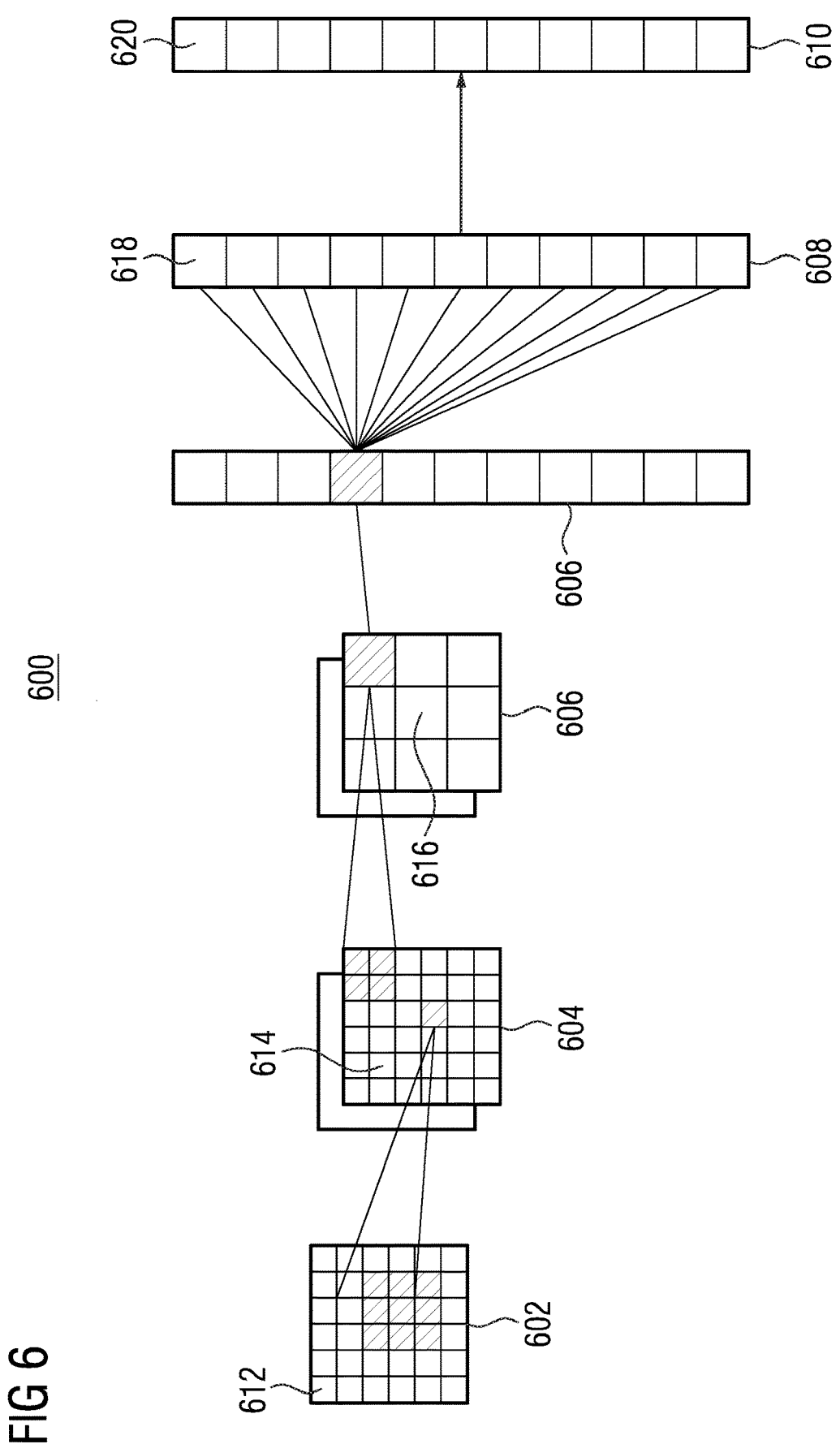
FIG. 6 shows a convolutional neural network that may be used to implement one or more embodiments.

FIG. 6 shows a convolutional neural network 600, in accordance with one or more embodiments. Machine learning networks described herein, such as, e.g., the machine learning based model implementing IMA 102, CDMA 104, and KMA 106 in FIG. 1, may be implemented using convolutional neural network 600.

In the embodiment shown in FIG. 6, the convolutional neural network comprises 600 an input layer 602, a convolutional layer 604, a pooling layer 606, a fully connected layer 608, and an output layer 610. Alternatively, the convolutional neural network 600 can comprise several convolutional layers 604, several pooling layers 606, and several fully connected layers 608, as well as other types of layers. The order of the layers can be chosen arbitrarily, usually fully connected layers 608 are used as the last layers before the output layer 610.

In particular, within a convolutional neural network 600, the nodes 612-620 of one layer 602-610 can be considered to be arranged as a d-dimensional matrix or as a d-dimensional image. In particular, in the two-dimensional case the value of the node 612-620 indexed with i and j in the n-th layer 602-610 can be denoted as $x^{(n)}_{[i,j]}$. However, the arrangement of the nodes 612-620 of one layer 602-610 does not have an effect on the calculations executed within the convolutional neural network 600 as such, since these are given solely by the structure and the weights of the edges.

In particular, a convolutional layer 604 is characterized by the structure and the weights of the incoming edges forming a convolution operation based on a certain number of kernels. In particular, the structure and the weights of the incoming edges are chosen such that the values $x^{(n)}_k$ of the nodes 614 of the convolutional layer 604 are calculated as a convolution $x^{(n)}_k = K_k * x^{(n-1)}$ based on the values $x^{(n-1)}$ of the nodes 612 of the preceding layer 602, where the convolution * is defined in the two-dimensional case as $$x_k^{(n)}[i,j] = (K_k * x^{(n-1)})[i,j] = \Sigma_i \Sigma_j K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 612-618 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 612-620 in the respective layer 602-610. In particular, for a convolutional layer 604, the number of nodes 614 in the convolutional layer is equivalent to the number of nodes 612 in the preceding layer 602 multiplied with the number of kernels.

If the nodes 612 of the preceding layer 602 are arranged as a d-dimensional matrix, using a plurality of kernels can be interpreted as adding a further dimension (denoted as "depth" dimension), so that the nodes 614 of the convolutional layer 604 are arranged as a (d+1)-dimensional matrix. If the nodes 612 of the preceding layer 602 are already arranged as a (d+1)-dimensional matrix comprising a depth dimension, using a plurality of kernels can be interpreted as expanding along the depth dimension, so that the nodes 614 of the convolutional layer 604 are arranged also as a (d+1)-dimensional matrix, wherein the size of the (d+1)-dimensional matrix with respect to the depth dimension is by a factor of the number of kernels larger than in the preceding layer 602.

The advantage of using convolutional layers 604 is that spatially local correlation of the input data can exploited by enforcing a local connectivity pattern between nodes of adjacent layers, in particular by each node being connected to only a small region of the nodes of the preceding layer.

In embodiment shown in FIG. 6, the input layer 602 comprises 36 nodes 612, arranged as a two-dimensional 6×6 matrix. The convolutional layer 604 comprises 72 nodes 614, arranged as two two-dimensional 6×6 matrices, each of the two matrices being the result of a convolution of the values of the input layer with a kernel. Equivalently, the nodes 614 of the convolutional layer 604 can be interpreted as arranges as a three-dimensional 6×6×2 matrix, wherein the last dimension is the depth dimension.

A pooling layer 606 can be characterized by the structure and the weights of the incoming edges and the activation function of its nodes 616 forming a pooling operation based on a non-linear pooling function f. For example, in the two dimensional case the values $x^{(n)}$ of the nodes 616 of the pooling layer 606 can be calculated based on the values $x^{(n-1)}$ of the nodes 614 of the preceding layer 604 as $$x^{(n)}[i,j]=f(x^{(n-1)}[id_1,jd_2], \ldots, x^{(n-1)}[id_1+d_1-1, jd_2+d_2-1])$$

In other words, by using a pooling layer 606, the number of nodes 614, 616 can be reduced, by replacing a number d1·d2 of neighboring nodes 614 in the preceding layer 604 with a single node 616 being calculated as a function of the values of said number of neighboring nodes in the pooling layer. In particular, the pooling function f can be the max-function, the average or the L2-Norm. In particular, for a pooling layer 606 the weights of the incoming edges are fixed and are not modified by training.

The advantage of using a pooling layer 606 is that the number of nodes 614, 616 and the number of parameters is reduced. This leads to the amount of computation in the network being reduced and to a control of overfitting.

In the embodiment shown in FIG. 6, the pooling layer 606 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 608 can be characterized by the fact that a majority, in particular, all edges between nodes 616 of the previous layer 606 and the nodes 618 of the fully-connected layer 608 are present, and wherein the weight of each of the edges can be adjusted individually.

In this embodiment, the nodes 616 of the preceding layer 606 of the fully-connected layer 608 are displayed both as two-dimensional matrices, and additionally as non-related nodes (indicated as a line of nodes, wherein the number of nodes was reduced for a better presentability). In this embodiment, the number of nodes 618 in the fully connected layer 608 is equal to the number of nodes 616 in the preceding layer 606. Alternatively, the number of nodes 616, 618 can differ.

Furthermore, in this embodiment, the values of the nodes 620 of the output layer 610 are determined by applying the Softmax function onto the values of the nodes 618 of the preceding layer 608. By applying the Softmax function, the sum the values of all nodes 620 of the output layer 610 is 1, and all values of all nodes 620 of the output layer are real numbers between 0 and 1.

A convolutional neural network 600 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 600 can be trained based on the backpropagation algorithm. For preventing overfitting, methods of regularization can be used, e.g. dropout of nodes 612-620, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 2. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 2, may be performed by a client computer in a network-based cloud computing system. The steps or functions of the methods and workflows described herein, including one or more of the steps of FIG. 2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 2, may be implemented using one or more computer programs that are executable by such a processor.

A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 7:
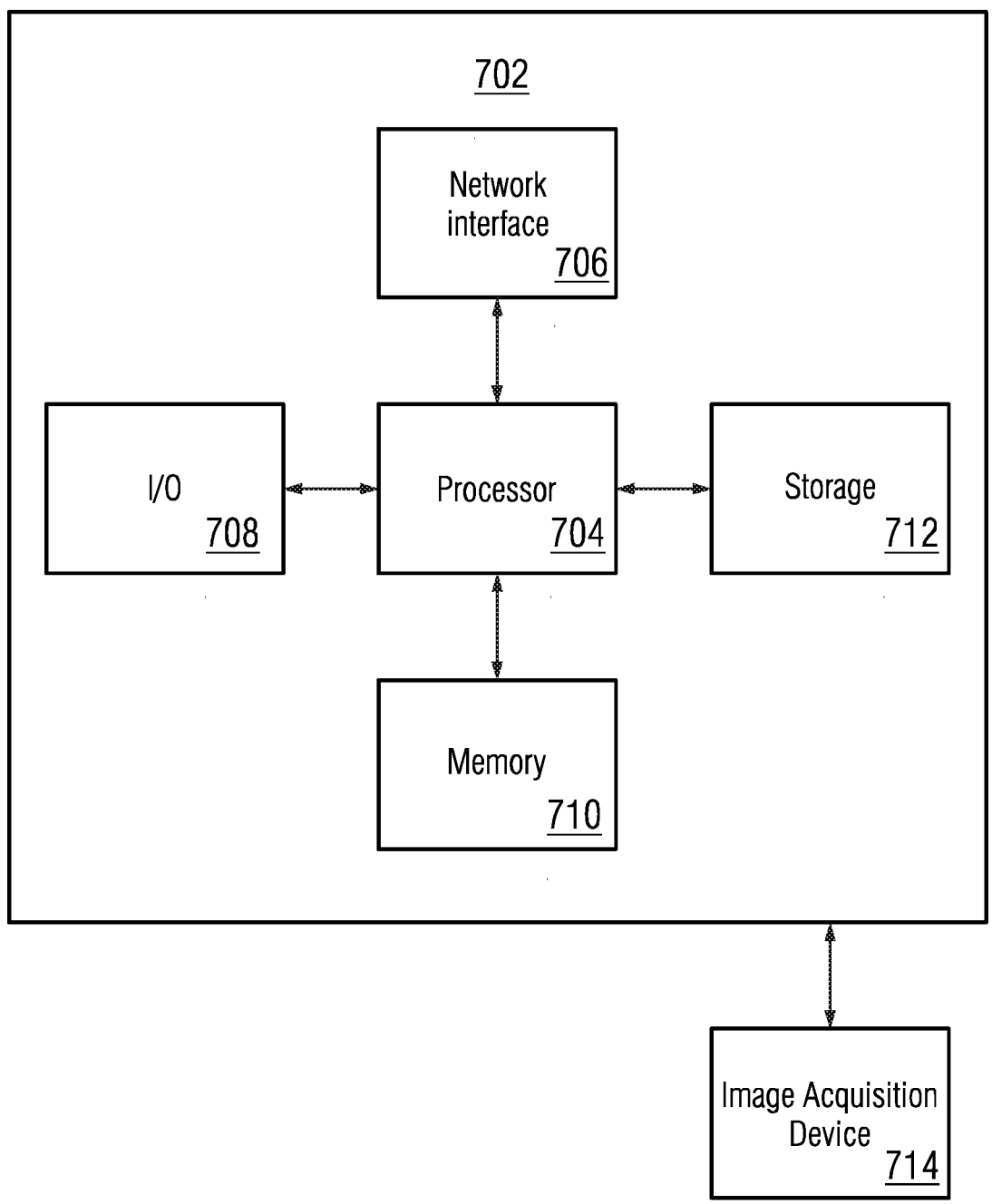
FIG. 7 shows a high-level block diagram of a computer that may be used to implement one or more embodiments.

A high-level block diagram of an example computer 702 that may be used to implement systems, apparatus, and methods described herein is depicted in FIG. 7. Computer 702 includes a processor 704 operatively coupled to a data storage device 712 and a memory 710. Processor 704 controls the overall operation of computer 702 by executing computer program instructions that define such operations. The computer program instructions may be stored in data storage device 712, or other computer readable medium, and loaded into memory 710 when execution of the computer program instructions is desired. Thus, the method and workflow steps or functions of FIG. 2 can be defined by the computer program instructions stored in memory 710 and/or data storage device 712 and controlled by processor 704 executing the computer program instructions. For example, the computer program instructions can be implemented as computer executable code programmed by one skilled in the art to perform the method and workflow steps or functions of FIG. 2. Accordingly, by executing the computer program instructions, the processor 704 executes the method and workflow steps or functions of FIG. 2. Computer 702 may also include one or more network interfaces 706 for communicating with other devices via a network. Computer 702 may also include one or more input/output devices 708 that enable user interaction with computer 702 (e.g., display, keyboard, mouse, speakers, buttons, etc.).

Processor 704 may include both general and special purpose microprocessors, and may be the sole processor or one of multiple processors of computer 702. Processor 704 may include one or more central processing units (CPUs), for example. Processor 704, data storage device 712, and/or memory 710 may include, be supplemented by, or incorporated in, one or more application-specific integrated circuits (ASICs) and/or one or more field programmable gate arrays (FPGAs).

Data storage device 712 and memory 710 each include a tangible non-transitory computer readable storage medium. Data storage device 712, and memory 710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 708 may include peripherals, such as a printer, scanner, display screen, etc. For example, input/output devices 708 may include a display device such as a cathode ray tube (CRT) or liquid crystal display (LCD) monitor for displaying information to the user, a keyboard, and a pointing device such as a mouse or a trackball by which the user can provide input to computer 702.

Any or all of the systems and apparatus discussed herein, IMA 102, CDMA 104, and KMA 106 of FIG. 1, may be implemented using one or more computers such as computer 702.

One skilled in the art will recognize that an implementation of an actual computer or computer system may have other structures and may contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for automatically determining an assessment of a patient, comprising:
   automatically interacting with a patient, by a first trained machine learning based model guided by a second trained machine learning based model, to acquire initial patient data;
   automatically retrieving, by a third trained machine learning based model guided by the second trained machine learning based model, health related information from one or more databases;
   automatically determining one or more risk factors associated with the patient, by the second trained machine learning based model, based on the acquired initial patient data and the retrieved health related information;
   presenting a consolidated information view of the one or more risk factors to the patient via a display device;
   automatically interacting with the patient, by the first trained machine learning based model guided by the second trained machine learning based model, using the presented consolidated information view to acquire additional patient data based on 1) the one or more determined risk factors and 2) data required by one or more physiology models of the patient for simulating one or more clinical scenarios;
   updating the presented consolidated information view of the one or more risk factors based on the additional patient data as the additional patient data is acquired;
   automatically determining the assessment of the patient, by the second trained machine learning based model, based on the initial patient data and the additional patient data using the one or more physiology models simulating the one or more clinical scenarios; and
   displaying the assessment of the patient on the display device.

2. The method of claim 1, wherein automatically determining the assessment of the patient, by the second trained machine learning based model, based on the initial patient data and the additional patient data using the one or more physiology models simulating the one or more clinical scenarios comprises:

processing the initial patient data and the additional patient data into a particular format; and inputting the processed initial patient data and the processed additional patient data into the one or more physiology models of the patient.

3. The method of claim 1, wherein automatically determining the assessment of the patient, by the second trained machine learning based model, based on the initial patient data and the additional patient data using the one or more physiology models simulating the one or more clinical scenarios comprises:

determining the assessment of the patient with an associated level of confidence.

4. The method of claim 1, wherein automatically determining the assessment of the patient, by the second trained machine learning based model, based on the initial patient data and the additional patient data using the one or more physiology models simulating the one or more clinical scenarios comprises:

determining a diagnosis for a medical condition associated with the patient.

5. The method of claim 1, wherein automatically determining the assessment of the patient, by the second trained machine learning based model, based on the initial patient data and the additional patient data using the one or more physiology models simulating the one or more clinical scenarios comprises:

determining a recommended course of action for the patient.

6. The method of claim 1, wherein the one or more risk factors comprises at least one of genetic risk factors, environmental risk factors, and lifestyle related risk factors.

7. The method of claim 1, wherein automatically interacting with the patient, by the first trained machine learning based model guided by the second trained machine learning based model, using the presented consolidated information view to acquire additional patient data based on 1) the one or more determined risk factors and 2) data required by one or more physiology models of the patient for simulating one or more clinical scenarios comprises:

asking questions to the patient and receiving answers from the patient.

8. The method of claim 1, wherein automatically interacting with the patient, by the first trained machine learning based model guided by the second trained machine learning based model, using the presented consolidated information view to acquire additional patient data based on 1) the one or more determined risk factors and 2) data required by one or more physiology models of the patient for simulating one or more clinical scenarios comprises:

retrieving clinical measurements of the patient.

9. An apparatus for automatically determining an assessment of a patient, comprising:

means for automatically interacting with a patient, by a first trained machine learning based model guided by a second trained machine learning based model, to acquire initial patient data;

means for automatically retrieving, by a third trained machine learning based model guided by the second trained machine learning based model, health related information from one or more databases;

means for automatically determining one or more risk factors associated with the patient, by the second trained machine learning based model, based on the acquired initial patient data and the retrieved health related information;

means for presenting a consolidated information view of the one or more risk factors to the patient via a display device;

means for automatically interacting with the patient, by the first trained machine learning based model guided by the second trained machine learning based model, using the presented consolidated information view to acquire additional patient data based on 1) the one or more determined risk factors and 2) data required by one or more physiology models of the patient for simulating one or more clinical scenarios;

means for updating the presented consolidated information view of the one or more risk factors based on the additional patient data as the additional patient data is acquired;

means for automatically determining the assessment of the patient, by the second trained machine learning based model, based on the initial patient data and the additional patient data using the one or more physiology models simulating the one or more clinical scenarios; and means for displaying the assessment of the patient on the display device.

10. The apparatus of claim 9, wherein the means for automatically determining the assessment of the patient, by the second trained machine learning based model, based on the initial patient data and the additional patient data using the one or more physiology models simulating the one or more clinical scenarios comprises:

means for processing the initial patient data and the additional patient data into a particular format; and means for inputting the processed initial patient data and the processed additional patient data into the one or more physiology models of the patient.

11. The apparatus of claim 9, wherein the means for automatically determining the assessment of the patient, by the second trained machine learning based model, based on the initial patient data and the additional patient data using the one or more physiology models simulating the one or more clinical scenarios comprises:

means for determining the assessment of the patient with an associated level of confidence.

12. The apparatus of claim 9, wherein the means for automatically determining the assessment of the patient, by the second trained machine learning based model, based on the initial patient data and the additional patient data using the one or more physiology models simulating the one or more clinical scenarios comprises:

means for determining a diagnosis for a medical condition associated with the patient.

13. A non-transitory computer readable medium storing computer program instructions for automatically determining an assessment of a patient, the computer program instructions when executed by a processor cause the processor to perform operations comprising:

automatically interacting with a patient, by a first trained machine learning based model guided by a second trained machine learning based model, to acquire initial patient data;

automatically retrieving, by a third trained machine learning based model guided by the second trained machine learning based model, health related information from one or more databases;

automatically determining one or more risk factors associated with the patient, by the second trained machine learning based model, based on the acquired initial patient data and the retrieved health related information;

presenting a consolidated information view of the one or more risk factors to the patient via a display device;

automatically interacting with the patient, by the first trained machine learning based model guided by the second trained machine learning based model, using the presented consolidated information view to acquire additional patient data based on 1) the one or more determined risk factors and 2) data required by one or more physiology models of the patient for simulating one or more clinical scenarios;

updating the presented consolidated information view of the one or more risk factors based on the additional patient data as the additional patient data is acquired;

automatically determining the assessment of the patient, by the second trained machine learning based model, based on the initial patient data and the additional patient data using the one or more physiology models simulating the one or more clinical scenarios; and displaying the assessment of the patient on the display device.

14. The non-transitory computer readable medium of claim 13, wherein automatically determining the assessment of the patient, by the second trained machine learning based model, based on the initial patient data and the additional patient data using the one or more physiology models simulating the one or more clinical scenarios comprises:

determining a recommended course of action for the patient.

15. The non-transitory computer readable medium of claim 13, wherein the one or more risk factors comprises at least one of genetic risk factors, environmental risk factors, and lifestyle related risk factors.

16. The non-transitory computer readable medium of claim 13, wherein automatically interacting with the patient, by the first trained machine learning based model guided by the second trained machine learning based model, using the presented consolidated information view to acquire additional patient data based on 1) the one or more determined risk factors and 2) data required by one or more physiology models of the patient for simulating one or more clinical scenarios comprises:

asking questions to the patient and receiving answers from the patient.

17. The non-transitory computer readable medium of claim 13, wherein automatically interacting with the patient, by the first trained machine learning based model guided by the second trained machine learning based model, using the presented consolidated information view to acquire additional patient data based on 1) the one or more determined risk factors and 2) data required by one or more physiology models of the patient for simulating one or more clinical scenarios comprises:

retrieving clinical measurements of the patient.

* * * * *